(12) United States Patent
Maroney et al.

(10) Patent No.: US 6,736,851 B2
(45) Date of Patent: May 18, 2004

(54) MODULAR SHOULDER PROSTHESIS

(75) Inventors: Brian Maroney, Fort Wayne, IN (US); Jon M. Heckman, Warsaw, IN (US)

(73) Assignee: DePuy Orthopaedics, Inc., Warsaw, IN (US)

( * ) Notice: Subject to any disclaimer, the term of this patent is extended or adjusted under 35 U.S.C. 154(b) by 0 days.

(21) Appl. No.: 10/184,554

(22) Filed: Jun. 28, 2002

(65) Prior Publication Data

US 2004/0002765 A1 Jan. 1, 2004

(51) Int. Cl.$^7$ .................................................. A61F 2/40
(52) U.S. Cl. ................... 623/19.12; 623/19.11; 623/19.14; 623/23.4
(58) Field of Search ........................ 623/19.11, 19.12, 623/19.13, 19.14, 22.43, 22.44, 22.45, 22.46, 23.21, 23.4, 22.42, 22.41, 22.4, 22.2, 22.15, 22.11

(56) References Cited

U.S. PATENT DOCUMENTS

| | | | |
|---|---|---|---|
| 5,358,526 A | 10/1994 | Tornier | |
| 5,389,107 A | 2/1995 | Nassar et al. | |
| 5,658,340 A | 8/1997 | Müller et al. | |
| 5,702,457 A | * 12/1997 | Walch et al. | 623/19.13 |
| 5,702,486 A | 12/1997 | Craig et al. | |
| 5,741,335 A | 4/1998 | Gerber et al. | |
| 5,961,555 A | 10/1999 | Huebner | |
| 6,120,507 A | 9/2000 | Allard et al. | |
| 6,171,341 B1 | 1/2001 | Boileau et al. | |
| 6,197,062 B1 | 3/2001 | Fenlin | |
| 6,197,063 B1 | 3/2001 | Dews | |
| 6,206,925 B1 | 3/2001 | Tornier | |
| 6,228,120 B1 | 5/2001 | Lenard et al. | |
| 6,336,941 B1 | 1/2002 | Subba Rao et al. | |

FOREIGN PATENT DOCUMENTS

| | | |
|---|---|---|
| EP | 0 712 617 A1 | 5/1996 |
| EP | 0 715 836 A1 | 6/1996 |
| WO | WO 00/41653 | 7/2000 |

* cited by examiner

Primary Examiner—David J. Isabella
Assistant Examiner—Kamrin R. Landrem
(74) Attorney, Agent, or Firm—Maginot, Moore & Beck

(57) ABSTRACT

A shoulder prosthesis and/or prosthesis sizing system, especially for treatment of degenerative arthritis or trauma, has an articulating head component. The shoulder prosthesis includes a humeral stem and a series of humeral heads. The heads are attached to the humeral stem by means of a locking connector. The locking connector allows the humeral head to be oriented in multiple positions of version, varus/valgus angulation, eccentricity and head height, while providing rigid securing of the humeral head to the humeral stem in the selected position relative to the humeral stem. In one form, the locking connector includes an expansion collar that provides radially outward expansion for humeral head position locking. The present shoulder prosthesis provides a means to anatomically position the humeral head relative to the humeral stem and rigidly secure the humeral head in the selected position relative to the humeral stem. This is accomplished by a minimum of components.

22 Claims, 11 Drawing Sheets

MODULAR SHOULDER PROSTHESIS

BACKGROUND OF THE INVENTION

The present invention relates to prosthetic systems for the replacement of limbs or portions thereof. More particularly, the invention concerns a modular shoulder prosthesis system that can be used in the extremities that have experienced bone loss or significant, irreparable bone trauma.

For treatment of various problems with the shoulder such as degenerative arthritis and trauma of the shoulder, one method of providing relief to a patient is to replace the articulating surfaces of the shoulder, i.e. the humerus and glenoid articulating surfaces. In such replacement, pin relief, increased motion and anatomic reconstruction of the shoulder joint are goals of the orthopaedic surgeon. With multiple variations in human anatomy, prosthetic systems need to accurately replicated human anatomy with minimal component inventory.

Artificial or prosthetic joints for the extremities are well-known. Many of prosthetic joints are modular, meaning that they include a selection of different components to account for differences in patient anatomy or surgical procedures. For example, U.S. Patent No. 5,314,479, owned by the assignee of the present invention, discloses a modular shoulder prosthesis that includes an array of selectable stems, bodies, collars and head members. The modular prosthesis of the '479 Patent allows the orthopaedic surgeon to assemble a custom prosthetic joint by selecting different sizes, shapes and orientations of the individual joint components.

As indicated above, current modular prostheses consist of a series of humeral stems and heads for replacement of articulating surfaces. The stems are offered with various metaphysis and diaphysis sizes. Humeral heads are offered in various radiuses of curvature, diameters, and heights. Any locking member used to rigidly attach the humeral head to the humeral stem has a fixed position, offering no means for positional adjustment of version, varus/valgus angulation.

Eccentricity can be addressed using humeral heads with the attachment feature placed off center from the articulating exterior spherical surface. However, the eccentric position of the humeral head is only adjustable about the fixed central axis of the locking member located on the humeral stem. More importantly, version, varus/valgus angulation adjustments are not possible with these embodiments.

In view of the above-noted shortcomings, modular shoulder prostheses have been developed that allow orienting the humeral head in multiple angular positions. Each of these embodiments, however, is deficient in design, and thus each is considered a sub-optimal solution. In U.S. Pat. No. 6,197,062 issued to Fenlin provides a modular shoulder prosthesis that utilizes an offset male taper member. The offset male taper member is rotated about the connecting axis of the humeral stem thus changing the angular position of the humeral head. Some of the problems associated with this particular embodiment include having to completely remove the humeral head to make positional adjustments, and version and varus/valgus angulation adjustments are not independent of one another.

In EP 0712617, a modular shoulder prosthesis is provided that allows positional adjustments of the humeral head. This prosthesis utilizes a split spherical ball and locking set screw to rigidly secure the humeral head in the selected position. While independent adjustment of humeral head position is possible with this prosthesis, such adjustments to humeral head position can only be made when the humeral stem is removed from the humeral canal because of the location of the locking set screw.

In U.S. Pat. No. 5,741,335 and EP 0715836, a shoulder prosthesis is provided that has a locking member consisting of a split spherical ball and locking set screws. A humeral head with a spherical cavity receives the spherical ball. The locking set screws located on the lateral aspect of the humeral stem below the head resection plane advances a pusher that compresses the ball against the humeral head stem while locking the ball against the cavity to lock the humeral head in place. The location of the locking set screws make it impossible to remove the humeral head or make positional changes to the humeral head after the humeral stem is engaged in the bone.

With the above shoulder prostheses, once the shoulder prosthesis has been inserted into the patient's bone, the angular position of the humeral head cannot be changed without removing the humeral stem. Misalignment caused by such factors as incorrect resection are not readily correctable with respect to humeral head alignment.

Consequently, there is a need for a modular shoulder system that can accommodate differences in patient anatomy, particularly with respect to angular positioning of the humeral head with respect to the humeral stem. There is a further need for a shoulder prosthesis that provides version and varus/valgus angulation/positioning that is easily set and reset.

SUMMARY OF THE INVENTION

In order to address these needs, the present invention provides a shoulder prosthesis designed to meet the challenges of shoulder replacement surgery. In one embodiment, shoulder prosthesis comprises at least three components, namely a humeral stem, a humeral head, and an adjustment and/or humeral head locking device.

In one form, the subject invention provides a shoulder prosthesis. The shoulder prosthesis includes a humeral stem adapted to be implanted into a humerus and including an expansion receptor, a humeral head defining an articulation surface and a mounting cavity, and an expansion device cooperating with the mounting cavity and the expansion receptor to couple the humeral head to the humeral stem, the expansion device allowing angular positioning of the humeral head relative to the humeral stem and locking of a selected angular position of the humeral head relative to the humeral stem by expansion of the expansion device relative to the expansion receptor.

In another form, the subject invention provides a shoulder prosthesis. The shoulder prosthesis includes a humeral stem having a proximal end and a distal end, the proximal end having a post extending therefrom, the post having tapered threads extending essentially from said proximal end of the humeral stem to an end of said post, a humeral head having an articulation surface and a bottom surface, and a mounting cavity in the bottom surface, and an expansion member configured to be received in the mounting cavity and having a threaded bore adapted to be received on the threaded post, the expansion member allowing humeral head angulation and fixing of a selected humeral head position when the expansion member is advanced onto the threaded bore such that expansion member expands.

In yet another form, the subject invention provides a shoulder prosthesis. The shoulder prosthesis includes a humeral stem having a proximal end and a distal end, the proximal end having an expansion cavity therein, a humeral head having an articulation surface and a bottom surface, and a mounting cavity in the bottom surface, and an expansion device configured to be received in the expansion cavity, the expansion device having an expansion member with a threaded bore and a mounting expander, the mounting expander having a head adapted to receive the mounting cavity of the humeral head and a threaded body adapted to receive the expansion member, the expansion device allowing humeral head angulation and fixing of a selected humeral head position when the mounting expander is advanced onto the threaded bore such that expansion member expands.

DESCRIPTION OF THE FIGURES

Corresponding reference characters indicated corresponding parts throughout the figures.

DESCRIPTION OF THE PREFERRED EMBODIMENTS

Figure 1:
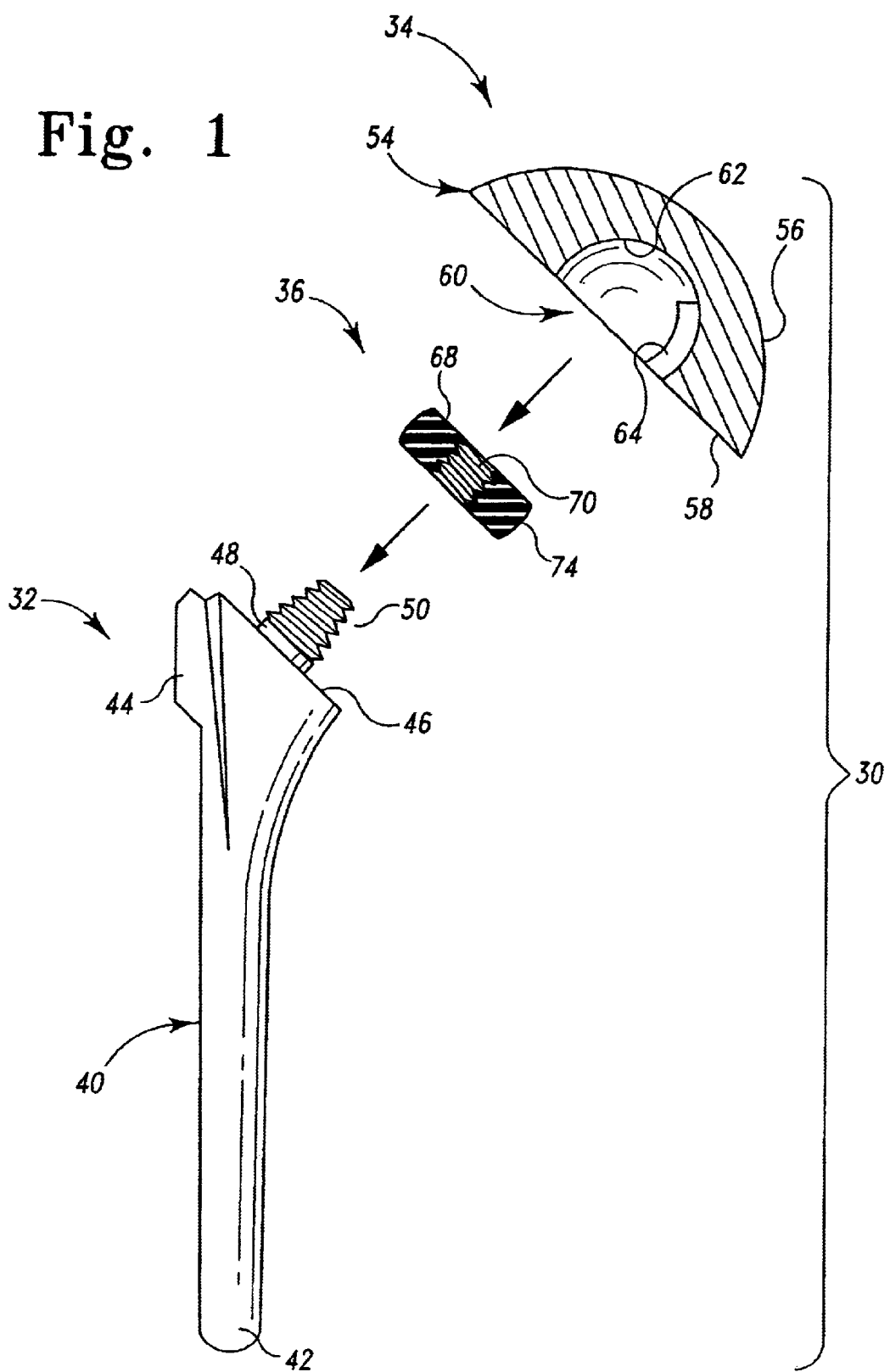
FIG. 1 is an exploded side view of a proximal humeral replacement or prosthesis assembled from components constituting a comprehensive modular limb preservation system in accordance with one embodiment of the present invention, some of the components of which are depicted in cross-section.

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

The present invention contemplates a limb preservation system that includes a comprehensive set of modular implants capable of addressing a wide range of orthopaedic conditions. Components of the system can be combined in a variety of ways to account for variations in patient anatomy and differences in bone or limb trauma. For instance, the comprehensive modular implant system of the present invention can be employed as a replacement for the proximal humerus. The particular modular components can be selected after consideration of the limb trauma, and more specifically in view of the degree and type of bone loss involved, such as might occur due to tumor, end-stage revision or trauma. Additionally, patient anatomy is utilized as a reference or model for selection of the particular size of components.

Referring to FIG. 1, there is depicted one embodiment of the subject invention. Particularly, there is depicted a shoulder prosthesis generally designated 30. It should be understood that the principles of the subject invention as described herein are applicable to prostheses for joints other than the shoulder, particularly for articulating surface joints similar to the shoulder. The shoulder prosthesis 30 includes a stem 32 configured, operable and/or adapted to be received in a humerus of a patient. The humeral stem 32 is implanted into a humerus such as is known in the art. The shoulder prosthesis 30 also includes a humeral head 34 that is receivable on the humeral stem 32. According to an aspect of the present invention, the humeral head 34 is selectively positionable regarding angular orientation with respect to the humeral stem 32, both in the version and varus/valgus angulation orientations. More particularly, the humeral head 34 is positionable in almost infinitely variable angular positions with respect to the humeral stem 32, whether the humeral stem 32 is implanted in the humerus or not.

The shoulder prosthesis 30 also includes a position locking mechanism 36 here embodied as a collar, ring or the like. As described below, the collar 36 cooperates with the humeral stem 32 and the humeral head 34 to provide a substantially universal joint for angular orientation of the humeral head 34 relative to the humeral stem 32 and for fixing or locking the selected angular orientation/position of the humeral head 34 relative to the humeral stem 32.

Figure 2:
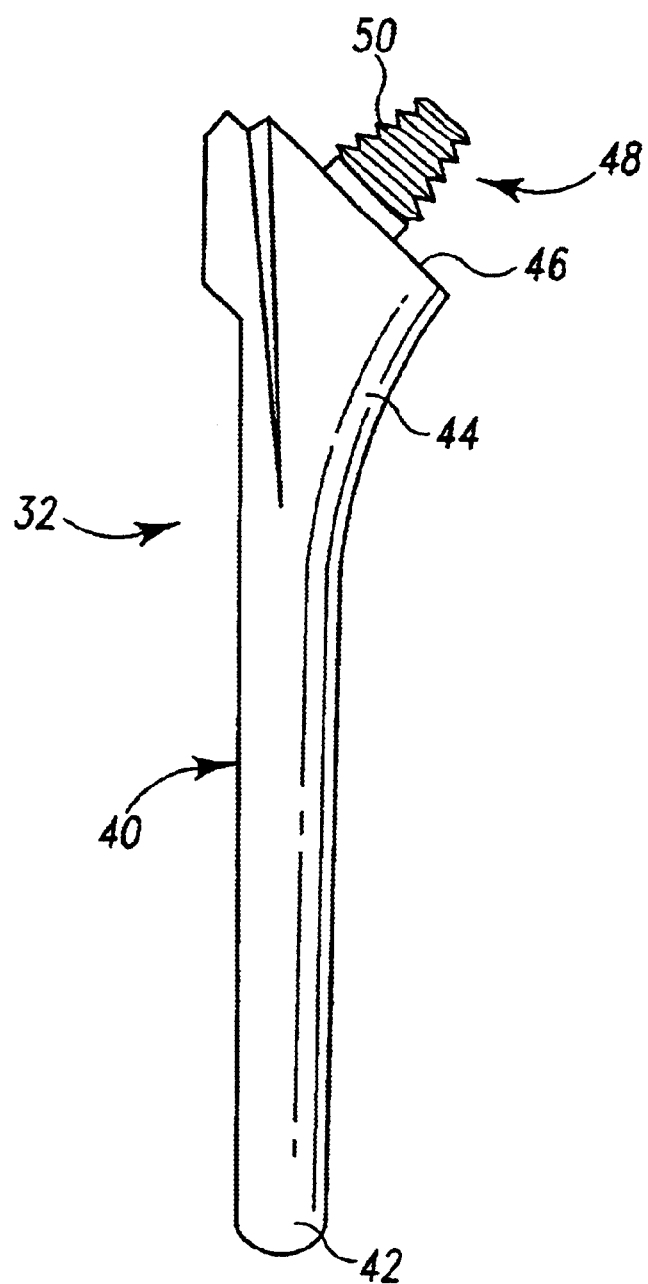
FIG. 2 is a side view of a humeral stem component of the humeral prosthesis of FIG. 1.

Referring now to FIG. 2, there is shown the humeral stem 32 of the shoulder prosthesis 30 of FIG. 1 and such will be described with more particularity. The humeral stem 32 is characterized by a body 40 having a distal end 42 and a proximal end 44. The body 40 is dimensioned to extend into the humeral canal of the patient's humerus. Particularly, the distal end 42 is inserted into a preferably previously reamed or bored humeral canal of the humerus (not shown). The body 40 also has an end surface 46 that is preferably substantially flat and provided at an angle relative to a longitudinal axis of the humeral stem 32. The angle of the end 46 is designed to match an angle of resection of the humerus. Note that the humeral stem 32 has no collar adjacent or proximate to the end 46. The humeral stem 32 is adapted to extend into the humeral canal such that the end 46 is flush with the resected surface of the humerus.

The humeral stem 32 also includes a hub, post, boss or the like 48 that extends from the end 46. As such, the humeral stem 32 may be considered a male component of the shoulder prosthesis 30. The post 48 includes threads 50 on an outer surface thereof. The post 48 is tapered inwardly as it extends outwardly from the end 46 and, as such, the threads 50 are tapered. In one form, the taper is of the same configuration as a Morse taper. The post 48 is preferably integral with the body 40.

Figure 3:
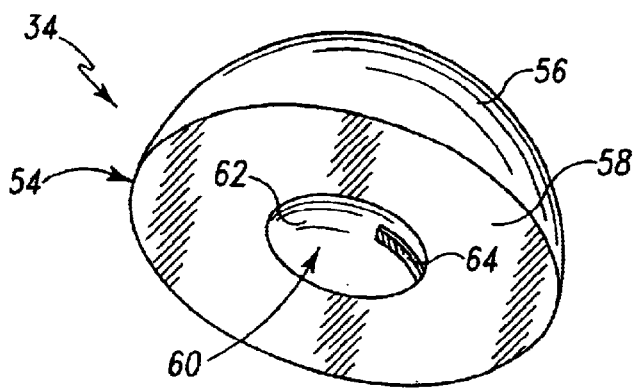
FIG. 3 is an enlarged bottom perspective view of a humeral head component of the humeral prosthesis of FIG. 1.
Figure 4:
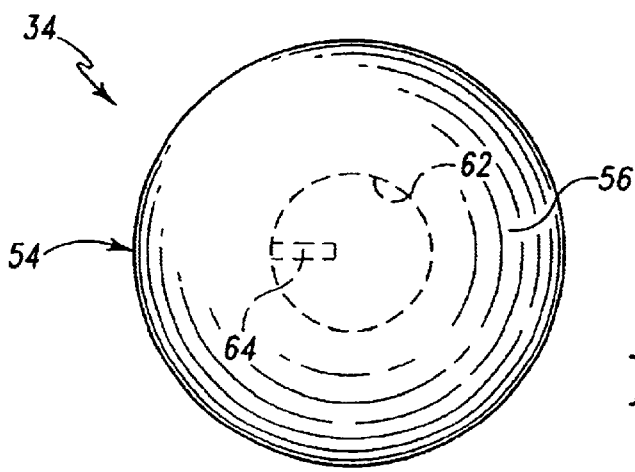
FIG. 4 is an enlarged top view of the humeral head component of FIG. 3.
Figure 5:
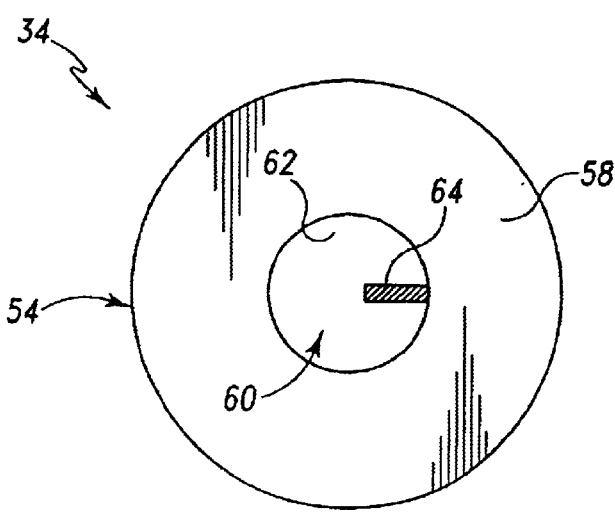
FIG. 5 is an enlarged bottom view of the humeral head component of FIG. 3.

Referring to FIGS. 3–5, there is shown the humeral head 34 of the shoulder prosthesis 30 of FIG. 1 and such will be described with more particularity. The humeral head 34 is characterized by a body 54 having an articulation surface 56 and a bottom surface 58. The articulation surface 56 is essentially hemispherically oblong in shape and/or a shape that closely matches the natural anatomy of the natural humerus head. The body 54 also includes a cavity 60 that extends into the body 54 from the bottom surface 58. The cavity 60 is essentially spherical and thus has an essentially spherical surface 62. While the cavity 60 is shown essentially centered in the body 54, it should be appreciated, and it is contemplated, that the cavity 60 may be provided in various locations or positions in the body 54. This permits the present invention to allow for eccentricity correction and/or compliance with respect to a patient's anatomy. By providing the cavity 60 in off center positions in the body 54, various eccentricities may be taken into account. The humeral head 34 comes in various dimensions with various cavity 60 locations.

The cavity 60 includes a key, rotation driver, angular adjustment guide and/or the like 64. The key 64 extends from the bottom surface 58 and along the spherical surface 62 to a point within the cavity 60. The length of the key 64 may be determined by the amount of angular displacement the humeral head 34 may undergo before bottoming out against the humeral stem 32, particularly the end surface 46 thereof. As developed more fully below, the key 34 in conjunction with the collar 36 provides a manner of adjusting the angular position or orientation (angulation) of the humeral head 34 relative to the humeral stem 32 and a manner of fixing or locking the humeral head 34 through rotation of the humeral head 34 in a manner described below. As an introduction, rotation of the humeral head 34 rotates the collar 36 which expands inside of the cavity 60 in connection with the advancing of the collar 36 upon the threaded, tapered post 48. Expansion of the collar 36 inside of the cavity 60 fixes the humeral head 34 from further angulation relative to the humeral stem 32.

Figure 6:
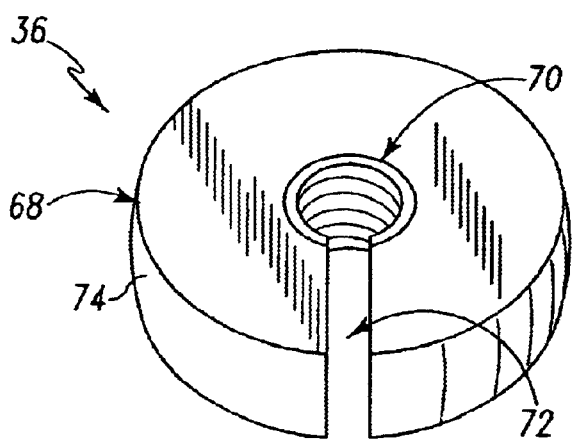
FIG. 6 is an enlarged top perspective view of an expansion collar component of the humeral prosthesis of FIG. 1.
Figure 7:
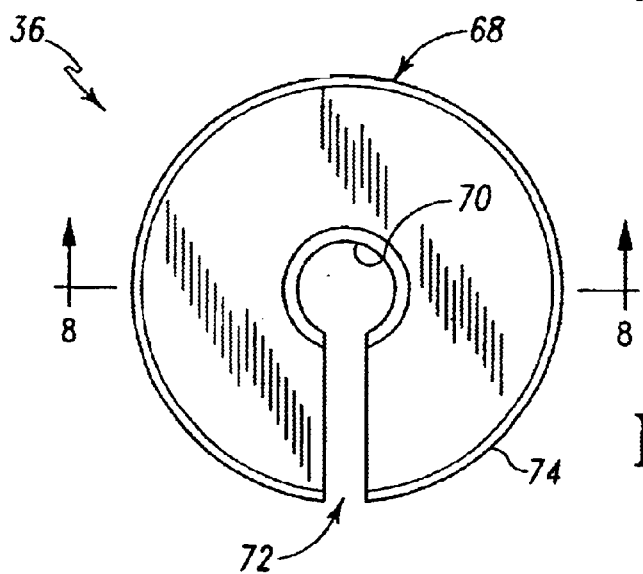
FIG. 7 is an enlarged top view of the expansion collar of FIG. 6.
Figure 8:
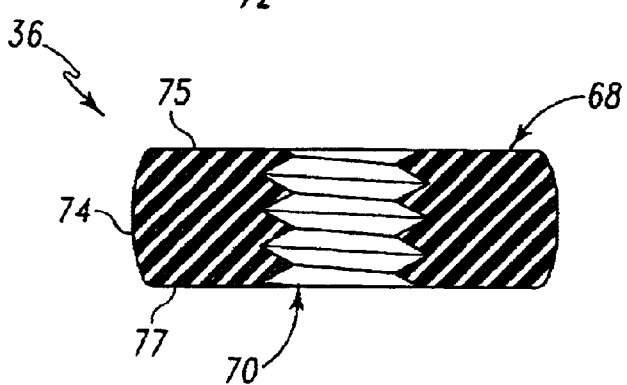
FIG. 8 is an enlarged sectional view of the expansion collar of FIG. 6 taken along line 8—8 of FIG. 7.

With reference to FIGS. 6–8, there is shown the collar 36 of the shoulder prosthesis 30 of FIG. 1 and such will be described with more particularity. The collar 36 is characterized by a body 68 defining an essentially annular ring having a bore 70 and an opening or gap 72. The collar 36 may be characterized as a non-overlapping split ring. The bore 70 is threaded with threading of the same dimensions as the threading 50 of the post 48 of the humeral stem 32 so as to threadedly mate with the threads 50. The gap 72 is sized to receive the key 64 therein and allow essentially arcuate movement of the key 64 therethrough.

As best seen in FIG. 8, the collar 36 has an outer, essentially annular surface 74 that has a radius of curvature extending from an arbitrary top 75 of the body 68 to an arbitrary bottom 77 of the body 68 of the collar 36 that matches the radius of curvature of the spherical cavity 60 of the humeral head 34. This allows the collar 36 to be received in the cavity 60. This also allows the collar 36 to angle in all directions with respect to an axis of rotation of the collar 36 (i.e. an axial axis through the bore 70) while within the cavity 60. As explained more fully below, since the collar 36 is fixed in position, the cooperating shapes of the cavity 60 and the outer surface 74 of the collar 36 allows the humeral head 34 to be angularly positionable about the collar 36.

Figure 9:
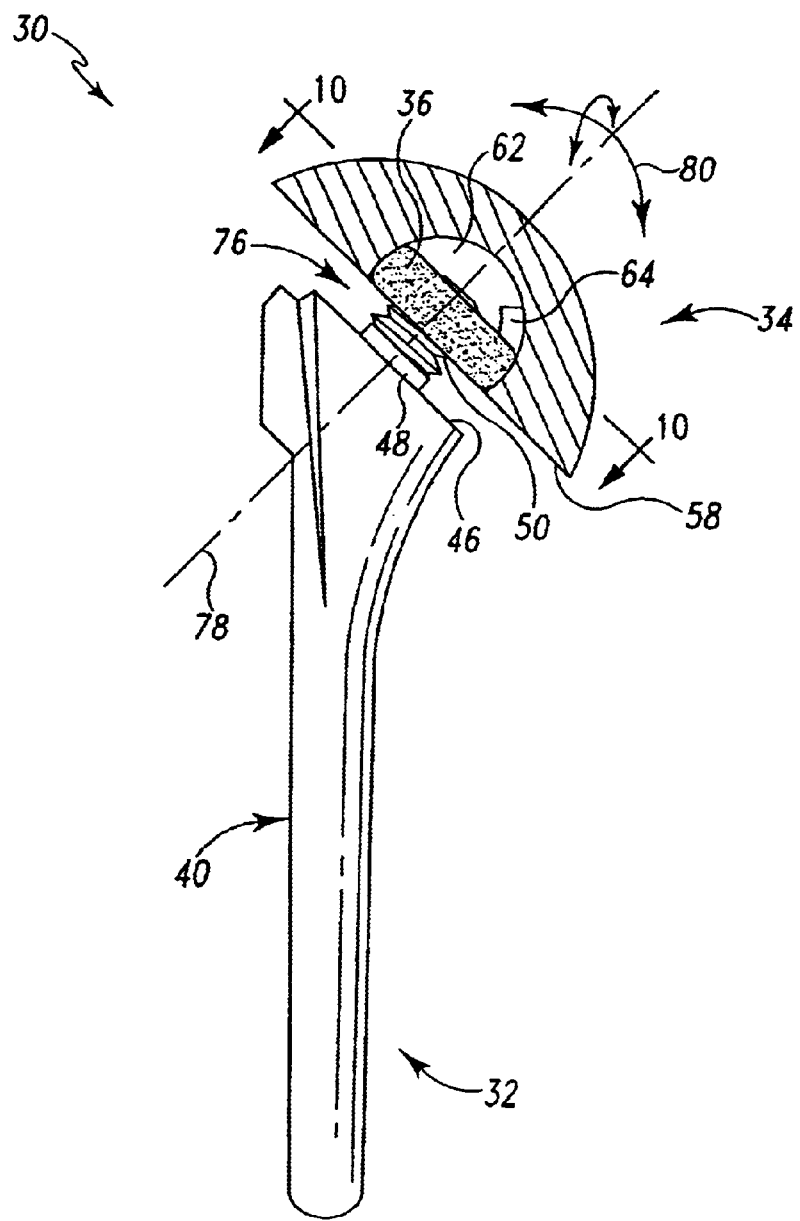
FIG. 9 is a side view of the proximal humeral prosthesis of FIG. 1 assembled, with the humeral head component of which is depicted in cross-section to better illustrate and/or understand the manner of articulation and expansion locking of the humeral head component relative to the humeral stem component.

Referring to FIG. 9, there is depicted the shoulder prosthesis 30 in an assembled state. The collar 36 is threadedly received on the threads 50 of the post 48 to provide a locking and angular adjustment mechanism 76. Because the threads 50 are tapered from smaller diameter threads at the top of the post 48 to larger diameter threads proximate the end 46, the collar 36 is first threadedly situated at the top of the post 48. The humeral head 34 is received over the collar 36. Particularly, the humeral head 34 is positioned such that the collar 36 is received in the cavity 60 and the side 74 of the collar 36 is in contact or immediately adjacent/congruent with the cavity surface 62 to the extent of the side 74. Additionally, the humeral head 34 is initially rotationally positioned such that the key 64 is received in the gap 72.

As illustrated by the arrows about the fixed axis 78 of the post 48, the humeral head 34 is free to perform version and varus/valgus angulation with respect to the humeral stem 32, and particularly with respect to the post 48 and/or the end surface 46 of the humeral stem 32. The double-headed arrow 80 indicates the movement of the humeral head 34 as the humeral head 34 is changed in angular orientation as constrained by the key 64 in the gap 72. The key 64 thus provides an angulation guide for the humeral head 34.

Figure 10:
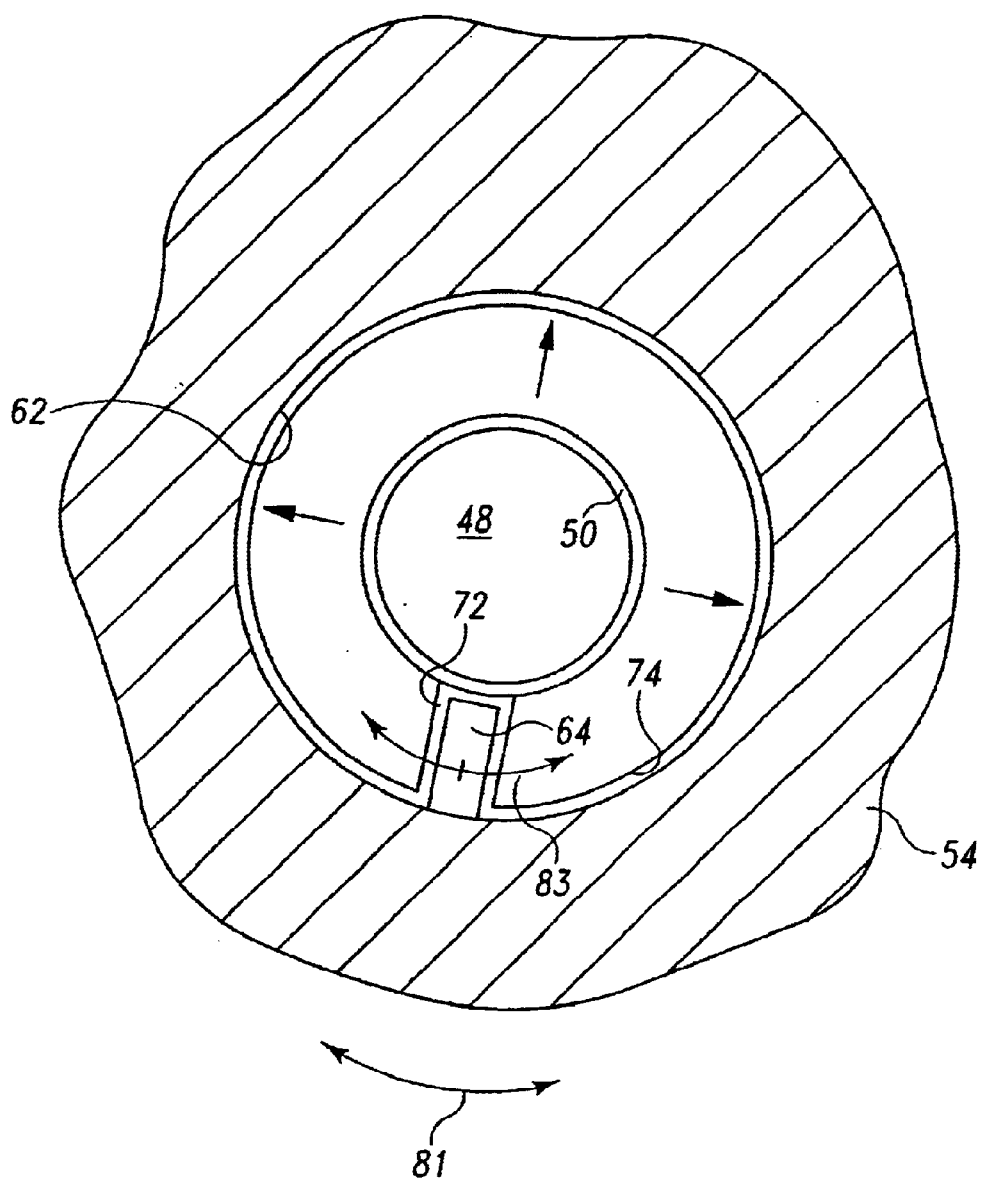
FIG. 10 is an enlarged cross sectional view of the humeral head component mounted onto the expansion collar and humeral stem component taken along line 10—10 of FIG. 9.

As depicted in FIG. 10, with reference being made thereto, the key 64 also provides a rotation driver for the collar 36 once the angulation of the humeral head 34 is complete. Rotational motion of the body 54 of the humeral head 34 in either direction, as indicated by the double-headed arrow 81, rotates the key 64 that engages a side of the gap 72 causing the collar 36 to rotate in the same direction of rotation as indicated by the double-headed arrow 83. Particularly, engagement of the key 64 with either end of the gap 72 rotates the collar 36 either advancing the collar 36 downward onto the post 48 or upwards off of the post 48. During advancement of the collar 36 downward onto the post 48, the taper of the post 48 radially outwardly pushes against the collar 36 (as indicated by the radially outward directed arrows). At a certain point of advancement of the collar 36 downward onto the post 48, the collar 36 is radially expanded outward wherein the side 74 of the collar 36 abuts the surface 62 of the cavity 60. Expansion of the collar 36 fixes the collar 36 within the cavity 60 and against movement with respect to the key 64. The humeral head 34 is then fixed in angular position. This can be accomplished by a strap wrench (not shown). To unfix the humeral head 34, the humeral head 34 is rotated in the opposite direction to the point where the radial outward expansion of the collar 36 eases from abutting the cavity surface 62. This can be accomplished either before or after implantation of the humeral stem 32. The present system thus allows the angular position of the humeral head 34 to be changed even after implantation, and as often as one desires.

Figure 11:
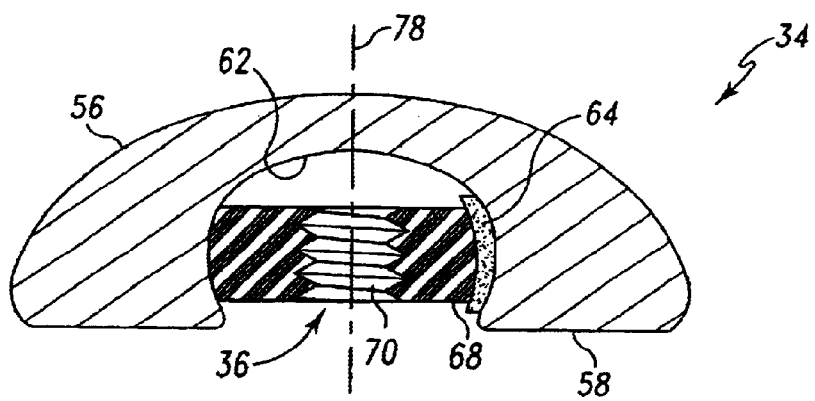
FIG. 11 is can enlarged cross-sectional view of the humeral head component and the expansion collar of the present invention illustrating a neutral position regarding a manner and degree of articulation by the humeral head component.
Figure 12:
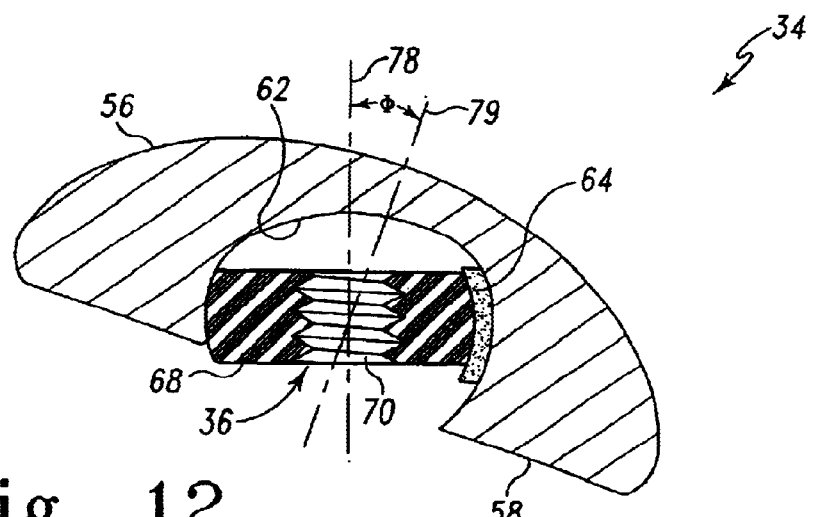
FIG. 12 an enlarged cross-sectional view of the humeral head component and the expansion collar of the present invention illustrating the manner and degree of articulation by the humeral head component relative to a right side of the humeral head component in a down position.
Figure 13:
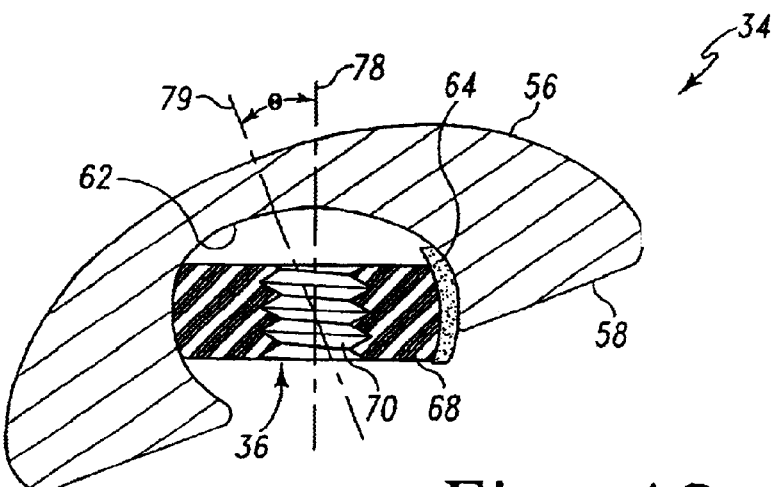
FIG. 13 an enlarged cross-sectional view of the humeral head component and the expansion collar of the present invention illustrating the manner and degree of articulation by the humeral head component relative to a left side of the humeral head component in a down position.

Referring to FIGS. 11–13, there is illustrated a neutral angulation positioning of the humeral head 34 as well as various extremes of angulation positioning of the humeral head 34 with respect to the collar 36. As indicated above, since the collar 36 is essentially fixed in position, the collar 36 may be considered fixed in position (while still free to rotate).

In FIG. 11, the collar 36 is in a neutral position. The humeral head 34 is oriented with respect to the collar 36 such that an axial axis of the humeral head 34 is coincident with the axial axis 78 of the collar 36.

In FIG. 12, the humeral head 34 is oriented with respect to the collar 36 such that an axial axis 79 of the humeral head 34 is offset by an angle φ from the collar axis 78. This illustrates angulation with respect to one direction.

In FIG. 13 the humeral head 34 is oriented with respect to the collar 36 such that the axial axis 79 of the humeral head 34 is offset by an angle Θ from the collar axis 78. This illustrates angulation with respect to another direction. The humeral head 34 is thus essentially infinitely variable within the angulation range. The collar 36 cooperates with the cavity 60 to provide an essential universal joint for angulation.

Figure 14:
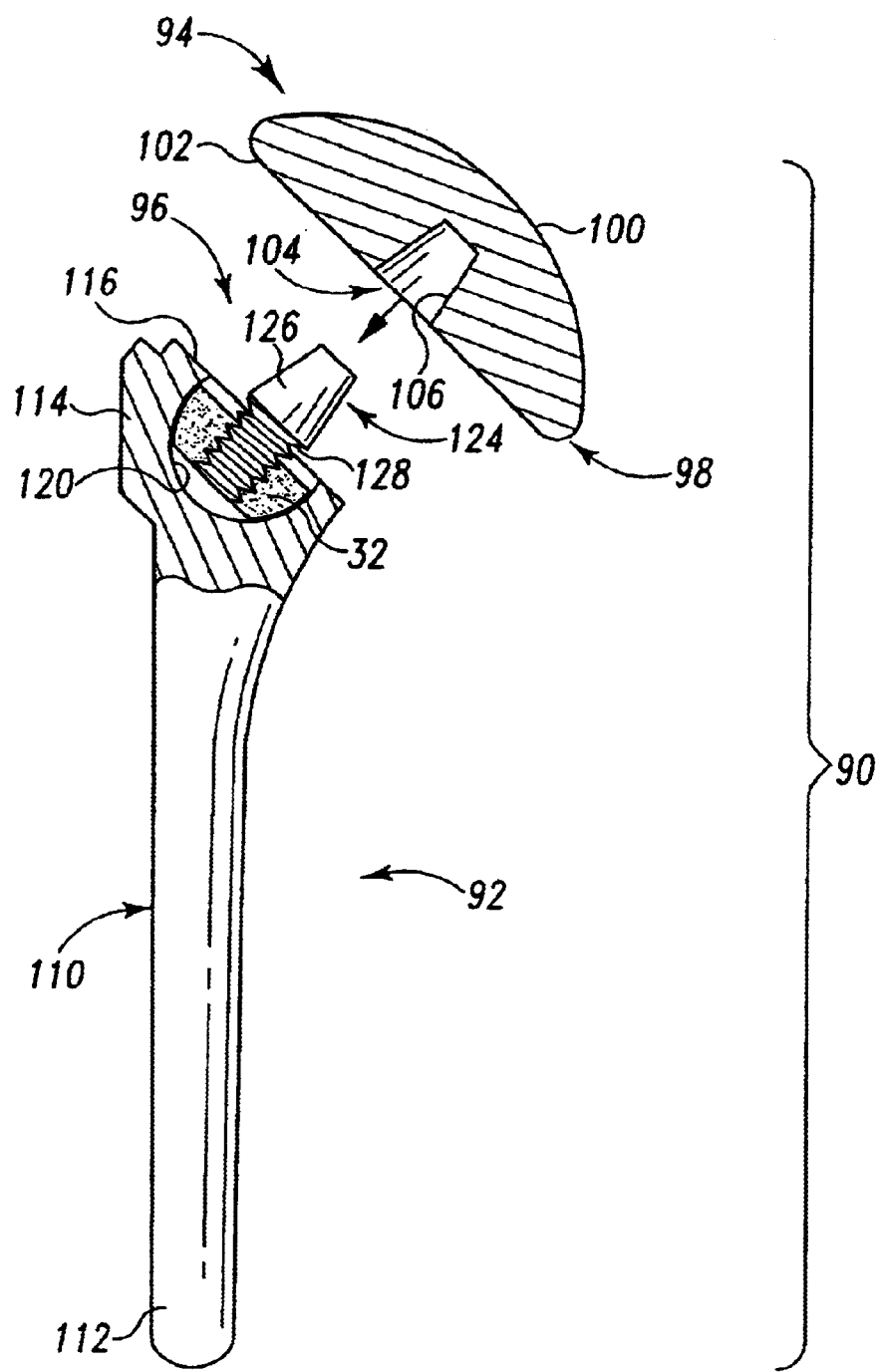
FIG. 14 is an exploded side view of a proximal humeral replacement or prosthesis assembled from components constituting a comprehensive modular limb preservation system in accordance with another embodiment of the present invention, some or a portion of the components of which are depicted in cross-section.

With reference now to FIG. 14, there is depicted another embodiment of a modular shoulder prosthesis generally designated 90. The shoulder prosthesis 90 includes a stem 92 configured, operable and/or adapted to be received in a humerus of a patient. The humeral stem 92 is implanted into a humerus such as is known in the art. The shoulder prosthesis 90 also includes a humeral head 94 that is receivable on the humeral stem 92. According to an aspect of the present invention, the humeral head 94 is selectively positionable regarding angular orientation with respect to the humeral stem 92, both in the version and varus/valgus angulation orientations. More particularly, the humeral head 94 is positionable in almost infinitely variable angular positions with respect to the humeral stem 92, whether the humeral stem 92 is implanted in the humerus or not.

The shoulder prosthesis 90 also includes a position locking mechanism 96 here embodied as a threaded post and a collar, ring or the like 36. As described below, the collar 36 cooperates with the adjustment hub or post 124, the humeral stem 92 and the humeral head 94 to provide a substantially universal joint for angular orientation of the humeral head 94 relative to the humeral stem 92 and for fixing or locking the selected angular orientation/position of the humeral head 94 relative to the humeral stem 92.

Figures 15, 16, 17:
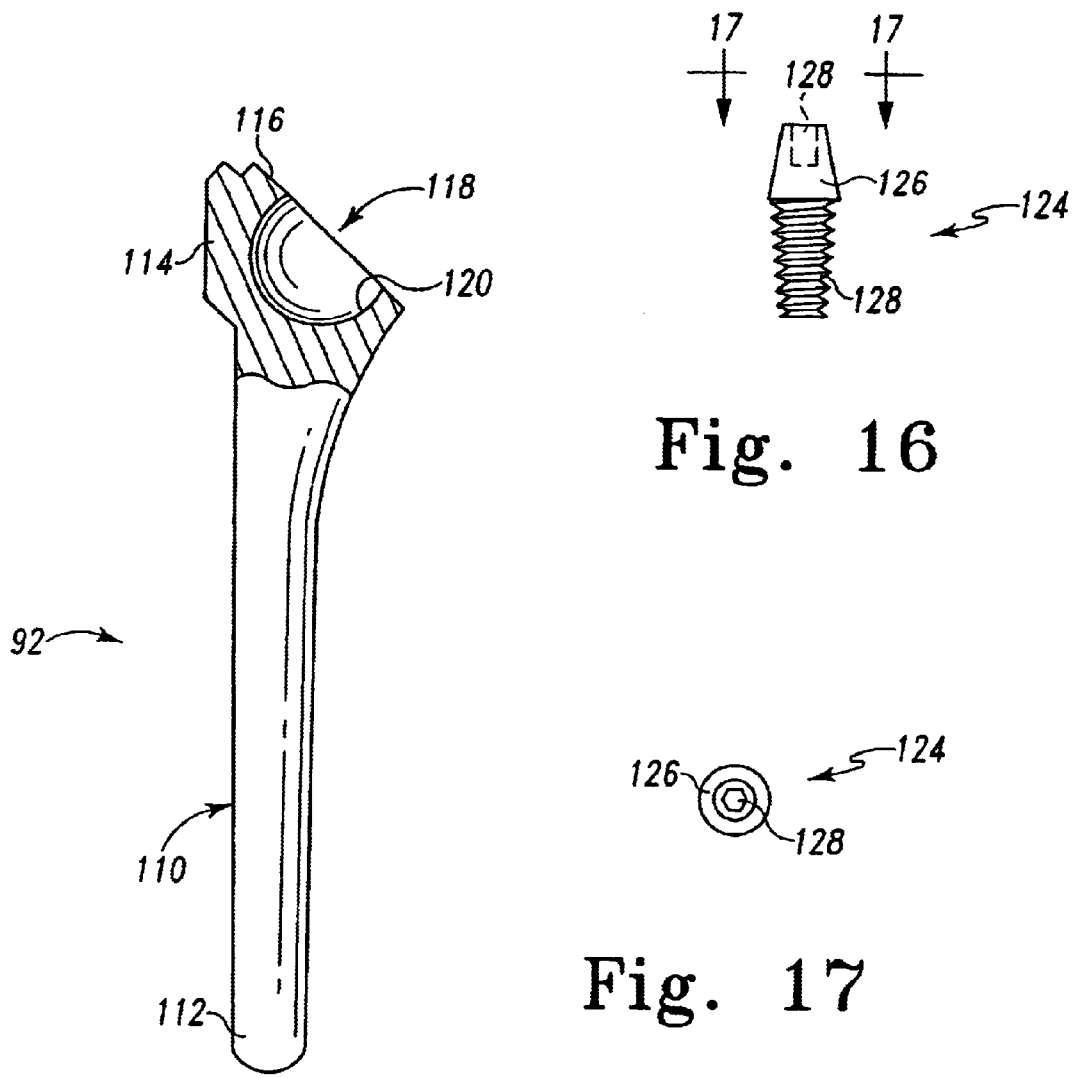
FIG. 15 is a side view of a humeral stem component of the humeral prosthesis of FIG. 14.
FIG. 16 is an enlarged side view of an integral locking and humeral head seating component of the humeral prosthesis of FIG. 14.
FIG. 17 is a top view of the integral locking and humeral head seating component of FIG. 16.

Referring now to FIG. 15, there is shown the humeral stem 92 of the shoulder prosthesis 90 of FIG. 14 and such will be described with more particularity. The humeral stem 92 is characterized by a body 110 having a distal end 112 and a proximal end 114. The body 110 is dimensioned to extend into the humeral canal of the patient's humerus. Particularly, the distal end 112 is inserted into a preferably previously reamed or bored humeral canal of the humerus (not shown). The body 110 also has an end surface 116 that is preferably substantially flat and provided at an angle relative to a longitudinal axis of the humeral stem 92. The angle of the end 116 is designed to match an angle of resection of the humerus. Note that the humeral stem 92 has no collar adjacent or proximate to the end 116. The humeral stem 92 is adapted to extend into the humeral canal such that the end 1 16 is flush with the resected surface of the humerus.

The humeral stem 92 also includes a recess or cavity that extends into the end 116. As such, the humeral stem 92 may be considered a female component of the shoulder prosthesis 90. The cavity 118 is substantially spherical in shape defined by an interior surface 120.

Referring back to FIG. 14 the humeral head 94 is characterized by a body 98 having an articulation surface 100 and a bottom surface 102. The articulation surface 100 is essentially hemispherically oblong in shape and/or a shape that closely matches the natural anatomy of the natural humerus head. The body 98 also includes a cavity or recess 104 that extends into the body 98 from the bottom surface 102. The cavity 104 is essentially frusto-conical and thus has an essentially frustoconical surface 106. Stated another way, the cavity 104 is cylindrically tapered into the body 98, preferably with a Morse type taper. While the cavity 104 is shown essentially centered in the body 98, it should be appreciated, and it is contemplated, that the cavity 104 may be provided in various locations or positions in the body 98. This permits the present invention to allow for eccentricity correction and/or compliance with respect to a patient's anatomy. By providing the cavity 104 in off center positions in the body 98, various eccentricities may be taken into account. The humeral head 94 comes in various dimensions with various cavity 104 locations.

Referring to FIGS. 16 and 17, the hub 124 is shown in particular detail. The hub 124 is characterized by a frusto-conical or tapered head 126 in like manner to the cavity 104 of the humeral head 94. This allows the humeral head 94 to be releasably mounted onto the hub 124. The hub 124 further includes a tapered and threaded body 128. The tapered and threaded body 128 is tapered opposite to the head 126. As best seen in FIG. 17, the head 126 includes a keyed opening 128 particularly for a allen wrench or the like. As explained further below, the hub 124 is rotated in the collar 36 in order to expand the collar 36 within the cavity 118 of the humeral stem 92. Expansion of the collar 36 provides locking of the collar 36 and hub 124 thus locking the humeral head 98.

Figure 18:
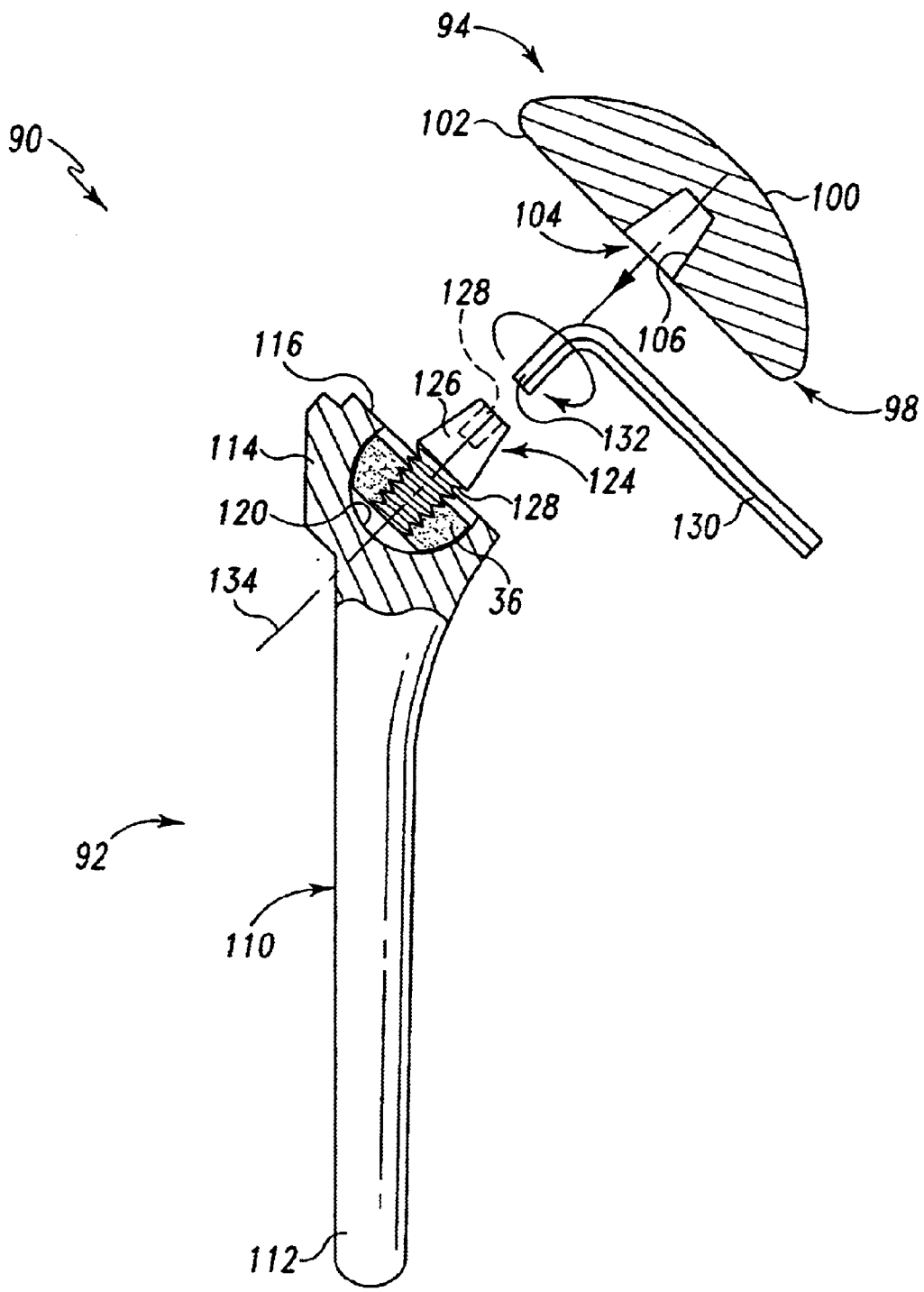
FIG. 18 is a partially exploded side view of the humeral prosthesis of FIG. 14 illustrating compression fixation of the integral locking and humeral head seating component before placement of the humeral head thereon.

Referring now to FIG. 18, there is depicted a manner of humeral head angulation positioning and/or locking thereof with respect to the shoulder prosthesis embodiment 90 of FIG. 14. It should initially be appreciated that the collar 32 operates in the same manner as that described above for the embodiment of FIG. 1. The collar 32 is situated in the cavity 118 such that the side of the collar 74 abuts and conforms to the spherical surface 120 of the cavity 118. This allows the collar 32 to be angularly positioned in the cavity 118. Once the angular position of the collar 32 is set (typically by temporarily placing the humeral head 94 onto the head 126, then removing same), the hub 124 is rotated (screwed) into the collar 32. Particularly, the threaded body 128 is received in the threaded bore 770 of the collar 32. A wrench 130 has a head 132 that is receivable in the opening 128 of the head 126. Rotation of the wrench 130 rotates the hub 124. As the hub advances into the collar 32, the taper of the threaded body 128 expands the collar 32. Expansion of the collar 32 wedges or fixes the collar 32 against the surface 120 of the cavity 118. Thereafter, the humeral head 94 is press fit onto the head 126 (i.e. the cavity 104 receives the head 126).

Figure 19:
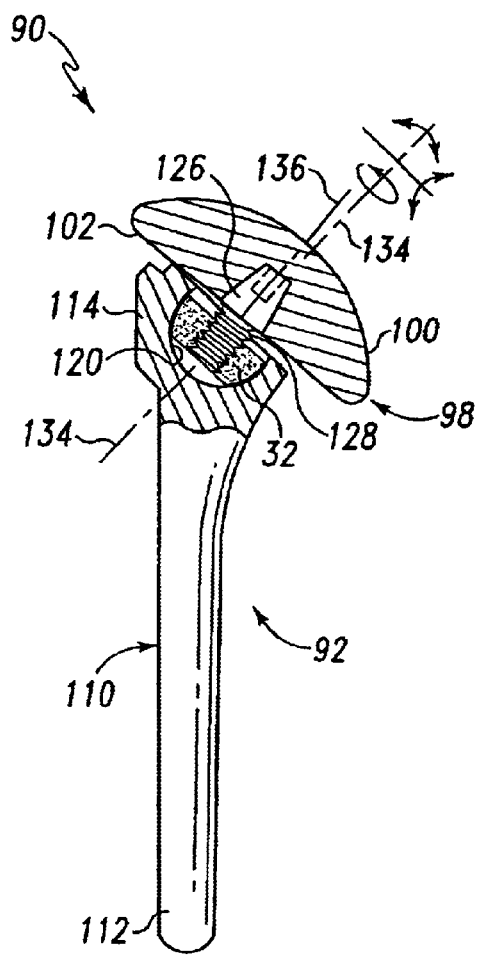
FIG. 19 is a side view of the proximal humeral prosthesis of FIG. 14 assembled, with the humeral head and stem components of which are depicted at least in partial cross-section to better illustrate and/or understand the manner of articulation and expansion locking of the humeral head component relative to the humeral stem component.

FIG. 19 depicts an example of an angular orientation of the humeral head 94 with respect to the humeral stem 92 for the modular shoulder prosthesis 90. In FIG. 19, the humeral head 94 is offset from an axis 134 of the cavity 118 of the humeral stem 92 as indicated by the axis line 136 for the humeral head 94. The arrows depict the possible angulation of the humeral head 94.

Figure 20:
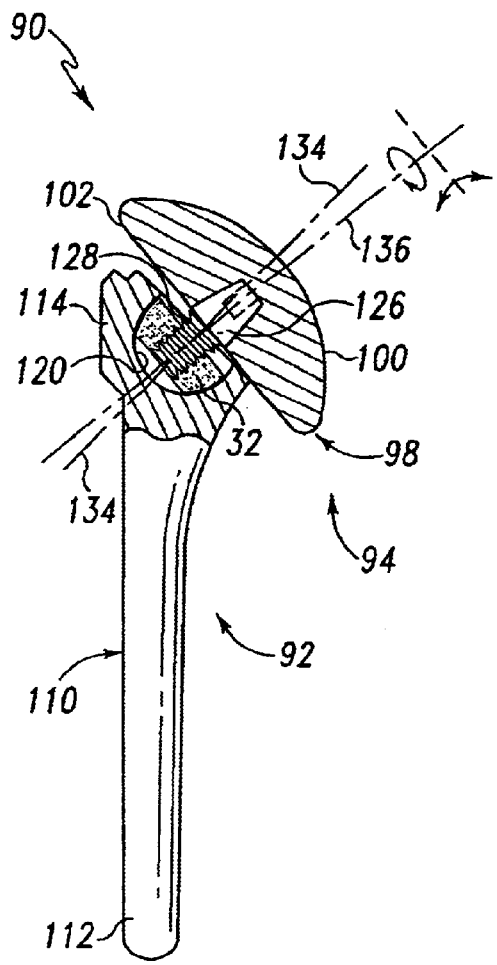
FIG. 20 is a side view of the proximal humeral prosthesis of FIG. 14 assembled, with the humeral head and stem components of which are depicted at least in partial cross-section to better illustrate and/or understand the manner of articulation and expansion locking of the humeral head component relative to the humeral stem component.

FIG. 20 depicts another example of an angular orientation of the humeral head 94 with respect to the humeral stem 92 for the modular shoulder prosthesis 90. In FIG. 20, the humeral head 94 is offset from an axis 134 of the cavity 118 of the humeral stem 92 as indicated by the axis line 136 for the humeral head 94. The arrows depict the possible angulation of the humeral head 94.

The components of the shoulder prosthesis can be formed of conventional bio-compatible metals or suitably strong materials. For instance, the humeral stem 32, humeral head 34 and the expansion ring 36 and/or the angular alignment locking mechanism can be formed of a titanium alloy. Such components may also be formed of a cobalt-chromium alloy.

The humeral stem 32 and the humeral head 34 porous coated depending upon the preferred application. The humeral stem 32 can be offered in conventional lengths and diameters. The humeral head 34

In one preferred embodiment, the shoulder prosthesis is provided to the orthopaedic surgeon in a kit of various sizes/dimensions of stems and heads, the stems and/or heads having centered and off-centered angular alignment cavities depending on the embodiment. The kit can include all of the components necessary to perform any of the replacement surgeries described above. The components can be assembled in the operating room, if necessary.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

What is claimed is:

1. A shoulder prosthesis comprising:
   a humeral stem adapted to be implanted into a humerus and including an expansion receptor;
   a humeral head defining an articulation surface and a mounting cavity; and
   an expansion device cooperating with said mounting cavity and said expansion receptor to couple said humeral head to said humeral stem, said expansion device allowing angular positioning of said humeral head relative to said humeral stem and locking of a selected angular position of said humeral head relative to said humeral stem by expansion of said expansion device relative to said expansion receptor,
   wherein said expansion device comprises an expansion ring having a threaded bore and an expansion gap, and
   wherein said expansion receptor comprises a post having a threaded taper, said threaded taper receiving said expansion ring such that when said expansion ring is advanced onto said threaded taper, said expansion ring expands.

2. The shoulder prosthesis of claim 1, wherein said humeral head includes a key within said mounting cavity, said key situated within said expansion gap of said expansion ring, said key translating rotational motion of said humeral head to said expansion ring to advance said expansion ring on said post to cause expansion of said expansion ring.

3. A shoulder prosthesis comprising:
   a humeral stem having a proximal end and a distal end, said proximal end having a post extending therefrom, said post having tapered threads extending essentially from said proximal end of said humeral stem to an end of said post;
   a humeral head having an articulation surface and a bottom surface, and a mounting cavity in said bottom surface; and
   an expansion member configured to be received in said mounting cavity and having a threaded bore adapted to be received on said threaded post, said expansion member allowing humeral head angulation and fixing of a selected humeral head position when said expansion member is advanced onto said threaded post such that said expansion member expands.

4. The shoulder prosthesis of claim 3, wherein said expansion member comprises an annular member having said threaded bore and an expansion gap.

5. The shoulder prosthesis of claim 4, wherein said mounting cavity has an essentially spherical-shaped surface, and said outside surface of said expansion has a like spherical-shaped surface.

6. The shoulder prosthesis of claim 4, wherein said mounting cavity includes a key, said key adapted to be situated within said expansion gap of said expansion member, said key translating rotational motion of said humeral head to said expansion member to advance said expansion member on said post to cause expansion of said expansion member.

7. The shoulder prosthesis of claim 6, wherein said key allows pivotal motion of said humeral head relative to said key articulating within said expansion gap.

8. A shoulder prosthesis, comprising:
   a humeral stem configured to be implanted in a humerus and having a threaded post that tapers from a first outer diameter to a second outer diameter, said first outer diameter being greater than said second outer diameter;
   a humeral head defining an articulation surface and having a mounting cavity;
   an expansion device positioned within said mounting cavity of said humeral head and defining a threaded opening configured to mate with said threaded post,
   wherein said threaded post defines an elongated post axis, and
   wherein rotation of said expansion device while said threaded opening of said expansion device is positioned in mating relationship with said threaded post causes said expansion device to move radially outwardly with respect to said axis of said threaded post.

9. The shoulder prosthesis of claim 8, wherein:
   said humeral head includes a cavity surface that defines said mounting cavity, and rotation of said expansion device while said threaded opening of said expansion device is positioned in mating relationship with said threaded post further causes an outer surface of said expansion device to be urged toward said cavity surface of said humeral head.

10. The shoulder prosthesis of claim 8, wherein:

said humeral stem includes a body from which said threaded post extends, said expansion device includes an annular collar defining a gap that extends from an outer sidewall thereof to an inner sidewall thereof, and said gap increases in size during rotation of said expansion device while said threaded opening of said expansion device is positioned in mating relationship with said threaded post.

11. The shoulder prosthesis of claim 10, wherein:

said humeral head includes a key member positioned within said mounting cavity, and said key member is positioned in said gap of said expansion device.

12. The shoulder prosthesis of claim 11, wherein:

said humeral head includes a cavity surface that defines said mounting cavity, and said key member extends from said cavity surface.

13. A prosthesis, comprising:

a prosthetic stem configured to be implanted in a bone and having a threaded post that tapers from a first outer diameter to a second outer diameter, said first outer diameter being greater than said second outer diameter;

a prosthetic head defining an articulation surface and having a mounting cavity;

an expansion device positioned within said mounting cavity of said prosthetic head and defining a threaded opening configured to mate with said threaded post, wherein said threaded post defines an elongalated post axis, and wherein rotation of said expansion device while said threaded opening of said expansion device is positioned in mating relationship with said threaded post causes said expansion device to move radially outwardly with respect to said axis of said threaded post.

14. The shoulder prosthesis of claim 13, wherein:

said prosthetic head includes a cavity surface that defines said mounting cavity, and rotation of said expansion device while said threaded opening of said expansion device is positioned in mating relationship with said threaded post further causes an outer surface of said expansion device to be urged toward said cavity surface of said humeral head.

15. The prosthesis of claim 13, wherein:

said prosthetic stem includes a body from which said threaded post extends, said expansion device includes an annular collar defining a gap that extends from an outer sidewall thereof to an inner sidewall thereof, and said gap increases in size during rotation of said expansion device while said threaded opening of said expansion device is positioned in mating relationship with said threaded post.

16. The prosthesis of claim 15, wherein:

said prosthetic head includes a key member positioned within said mounting cavity, and said key member is positioned in said gap of said expansion device.

17. The prosthesis of claim 16, wherein:

said prosthetic head includes a cavity surface that defines said mounting cavity, and said key member extends from said cavity surface.

18. A prosthesis, comprising:

a first prosthetic component having a threaded post that tapers from a first outer diameter to a second outer diameter, said first outer diameter being greater than said second outer diameter;

a second prosthetic having a mounting cavity; and an expansion device positioned within said mounting cavity of said second prosthetic component and defining a threaded opening configured to mate with said threaded post, wherein said threaded post defines an elongated post axis, and wherein rotation of said expansion device while said threaded opening of said expansion device is positioned in mating relationship with said threaded post causes said expansion device to move radially outwardly with respect to said axis of said threaded post.

19. The prosthesis of claim 18, wherein said first prosthetic component and said second prosthetic component are each selected from the group consisting of: a prosthetic head and a prosthetic stem.

20. The prosthesis of claim 19, wherein:

said expansion device includes an annular collar defining a gap that extends from an outer sidewall thereof to an inner sidewall thereof, and said gap increases in size during rotation of said expansion device while said threaded opening of said expansion device is positioned in mating relationship with said threaded post.

21. The prosthesis of claim 20, wherein:

said second prosthetic component includes a key member positioned within said mounting cavity, and said key member is positioned in said gap of said expansion device.

22. The prosthesis of claim 21, wherein:

said second prosthetic component includes a cavity surface that defines said mounting cavity, and said key member extends from said cavity surface.

* * * * *